United States Patent [19]
Cooper

[11] Patent Number: 5,836,904
[45] Date of Patent: Nov. 17, 1998

[54] ENHANCED COMFORT SLEEVE AND COVER FOR MEDICAL DEVICES AND SPORT PADS

[76] Inventor: Curtis R. Cooper, 3424 NW. 7th Pl., Gainesville, Fla. 32607

[21] Appl. No.: 593,271

[22] Filed: Jan. 29, 1996

[51] Int. Cl.⁶ ........................................... A61F 5/00
[52] U.S. Cl. .............................. 602/60; 602/26; 602/62; 602/63
[58] Field of Search ................... 602/20, 21, 23, 602/26, 60, 61, 62, 63, 13

[56] References Cited

U.S. PATENT DOCUMENTS

| | | | |
|---|---|---|---|
| 3,613,679 | 10/1971 | Bijou | 602/41 |
| 4,116,236 | 9/1978 | Albert | 602/26 |
| 4,870,956 | 10/1989 | Fatool et al. | 602/26 |
| 4,961,418 | 10/1990 | McLaurin-Smith | 602/21 |
| 5,168,577 | 12/1992 | Detty | 602/62 |
| 5,415,624 | 5/1995 | Williams | 602/21 |

*Primary Examiner*—Richard J. Apley
*Assistant Examiner*—Kim M. Lee
*Attorney, Agent, or Firm*—Sven W. Hanson

[57] ABSTRACT

The subject invention is an integral internal sleeve and external cover for use with medical support devices or protective sport pads. It provides an internal sleeve using cotton/elastomeric fabrics to provide a combination of improved comfort, greater shape and location retention. The combination of design and fabric provide improved protection for limbs from contact discomfort occurring with medical support devices and sport pads. An external cover is provided which fits snugly to the contours of the device or pad being covered. Fabrics providing attractive graphics are preferably used to improve the appearance of the device or pad. A simple design incorporating a thumb loop allows a user to attach the device without assistance.

3 Claims, 2 Drawing Sheets

ENHANCED COMFORT SLEEVE AND COVER FOR MEDICAL DEVICES AND SPORT PADS

BACKGROUND OF THE INVENTION

The subject invention pertains to the field of medical support devices such as splints and casts and the field of nonmedical and sport protective pads worn typically on a person's limbs. Specifically, the invention pertains to liners and coverings for such devices providing added comfort for the wearer as well as improved appearance.

Often medical support devices such as casts, splints and braces worn on a person's limbs are uncomfortable for the wearer due to the necessary hardness or roughness of the materials used. Devices worn for long periods of time may cause abrasions and contact bruising. This may be worsened by any roughness of texture. In addition, because the skin is covered, irritation is increased due to retained perspiration. For this reason cotton sock-like sleeves or liners are sometimes placed over an injured limb prior to applying a rigid cast. However, all cotton sock liners of this type may shift and bunch beneath a cast and also add to the unnatural and unsightly appearance of the cast.

Sport protective pads such as wrist pads worn by roller skate enthusiasts also suffer particularly from the problems of skin discomfort and absorbed perspiration. Because sport pads are worn during vigorous exercise, accumulation of sweat is a common problem. It also becomes necessary to wash such pads often due to the absorbed sweat. These pads are typically made of materials selected for durability. The roughness of such fabrics together with the substantial movements and actions inherent in roller skating and similar activities can lead to considerable skin discomfort.

The detracting appearance of medical support devices can effect the well being of the wearer. This has been addressed in the case of casts for children by the availability today of casting materials in a variety of colors. It is known that an attractive cast or brace will often be more accepted by a young wearer and reduce the negative psychological effects of wearing an obtrusive device. Appearance is also a factor for the adult wearers of medical devices but even more so with protective sport pads. Sport apparel is a major industry today and style and appearance of sporting equipment is a significant commercial consideration.

The subject invention is an integrated internal sleeve and external cover which provides both increased comfort for the wearer of medical support devices or sport pads as well as an enhanced appearance. It incorporates a novel design with innovative fabric application to create a device which satisfies multiple demands.

SUMMARY OF THE INVENTION

It is an object of the subject invention to provide an internal sleeve to be worn beneath medical support devices and sport pads worn on the arms or legs which assists in eliminating sweat and improves comfort for the wearer.

It is also an object of the invention to provide a replaceable external cover which may be worn over medical support devices and sport pads to improve the appearance of such devices and pads.

It is a further object of the invention to provide an integral internal sleeve and external cover for such devices and pads which will both provide increased comfort and enhanced appearance.

It is yet another object of the invention to provide a replaceable cover in a variety of graphical designs giving the wearer the ability to selectively determine the appearance of a device or pad worn on an arm or leg.

It is yet another object of the invention to provide an integral sleeve and cover which is easy to put on by the wearer without assistance of other persons.

It is an object of the invention to also provide an integral sleeve and cover which provides compression on the limb to treat medical conditions within the limb.

It is also an object of the invention to provide an internal sleeve and external cover which utilizes innovative fabrics to provide a combination of comfort and enhanced appearance. The invention design combines unique structural features to provide great ease of use and comfort while providing an attractive appearance to otherwise detracting devices.

The invention incorporates a generally tubular sleeve of fabric which is used to both underlie and cover a medical support device or protective sport pad worn on an arm or leg. The sleeve is formed of a tubular sleeve body which is drawn over the limb of the wearer prior to attaching the particular device or pad to be applied. After such a support device or pad is attached over a liner portion of the sleeve, a remaining cover portion of the sleeve body is folded back over the support device or pad. One advantage of an integral internal sleeve and external cover is improved stability of location. That is, the liner portion of the sleeve is less likely to slip away from beneath the support device or pad. Additionally, no separate fastener is required at the end of the device where the sleeve body is folded over the device or pad. The tubular sleeve body may be terminated in either a closure device or thumb loop or a combination of the two. The closure device may be integral to one end of the tubular sleeve body and may consist of a secured elastic which draws the sleeve body over the end of the device of pad. The loop may be formed by introducing a hole in the sleeve body or by securing a separate circle or hoop of fabric to the sleeve body end. In either case the loop is drawn, in use, over the wearer's finger or thumb to help secure the sleeve body to the limb. This particular mode is applicable when a cast, brace, or protective pad is to be applied to the forearm or wrist. The simplicity of this design allows for the wearer to easily put on the sleeve and cover without assistance by using the second hand. In another embodiment the invention includes multiple loops which may be drawn over a multiple of fingers to secure the sleeve in place.

When the sleeve is to be used under a support device or pad on a limb distant from the hand the loop feature is not applicable. In this case the sleeve is drawn over the device to be covered as previously described but is held in place solely by the terminating closure or fastener which draws the sleeve body around the end of the support device or pad. An alternative configuration may be used where the invention is to be worn under a flexible support device or pad applied to a knee or elbow. Here a cutout is provided to prevent discomfort due to rubbing when the joint is flexed.

The particular advantages of the present invention are accomplished by the application of modem cotton/elastomeric fabrics which combine the comfort of natural fibers with stretchability or elasticity. These fabrics create a liner which grips the limb as well as providing a cover which will fit snugly over the contours of a devise or pad creating a neat appearance. The preferred material is commonly available today as cotton-LYCRA®. These fabrics, in addition to acting as an efficient wick for perspiration, have a smooth yet soft texture or feel which provide comfort not found with other fabrics. Additionally, a soft, smooth, and wrinkle-free texture next to the skin is maintained with cotton/elastomeric fabrics even when wet with perspiration. These fabrics are also available in a broad variety of colors and patterns giving the wearer a multitude of possibilities in enhancing and improving the appearance of medical devices or sports pads.

An additional benefit of using LYCRA® or a similar fabric is the medically beneficial effects obtainable from skin compression which can be produced with elastomeric materials. Compressive outer garments are prescribed by doctors at times to treat medical conditions involving burns, scarring, and circulatory problems as well as others. A LYCRA® type fabric in the present invention can provide such a compression and an added benefit to the user. For such use the sleeve body may be formed of sufficiently small circumference to provide an effective compression when worn.

The claimed invention solves multiple problems of current medical support devices and protective sport pads. It uses a unique combination of design and materials to both increase the comfort for wearers of such devices while adding style and attractiveness to otherwise detracting attire.

DESCRIPTION OF THE PREFERRED EMBODIMENTS

Figure 1:
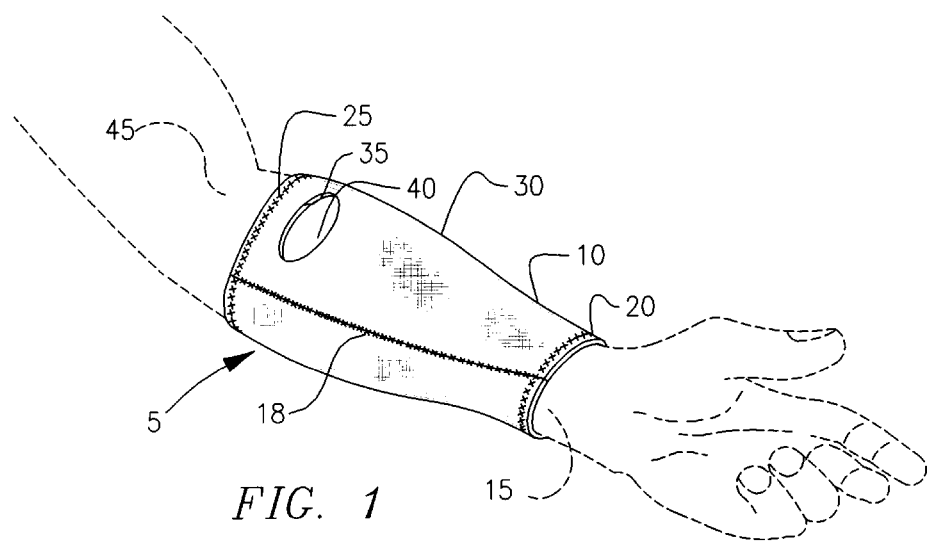
FIG. 1 shows one embodiment of the invention drawn onto a user's forearm prior to attaching a medical support device or sport pad.

FIG. 1 shows one embodiment of the invention drawn over a user's forearm prior to attaching a medical support device or protective sport pad. Henceforth, the term "support device" will be used in this specification to indicate medical support devices such as splints, braces, casts and similar medical body coverings as well as protective sport pads used to protect the body from contact injuries. The invention design is similarly motivated and equally applicable with all such devices. In FIG. 1, the invention consists of a generally tubular fabric sleeve body 5 which, in use, is first drawn over the arm of the user. After the sleeve body 5 is pulled onto the limb the particular support device to be used is then attached to the arm over a liner portion 10 of the sleeve body 5. The word "tubular" should not be construed as strictly meaning "circular" in cross section; because the sleeve body 5 is formed of nonrigid materials it is "tubular" in the same manner as the sleeve of a shirt. The liner portion 10 acts as a more comfortable barrier protecting the body from contact by the support device. When the sleeve body 5 is drawn over the limb it is positioned such that a sleeve body 5 first end opening 15 is located on the limb approximately at the position of one end of the support device as it will eventually be positioned. The sleeve body 5 is of sufficient length to provide a liner portion 10 sufficient to extend fully beneath a typical support device and provide a remaining length sufficient to cover the support device. The term "length" in this specification always refers to the distance or extent of the object parallel with the longitudinal axis of the human limb in consideration.

The sleeve body 5 is preferably formed from a generally rectangular shaped piece of fabric. Two opposing sides of the piece are drawn together and joined by stitching a longitudinal seam 18. The piece may be shaped with the opposing sides tapered relatively so that the resultant tubular shape has a varying circumference. This circumference should be slightly less than that of the limb over which the sleeve body 5 is to be worn. In this way a slightly snug fit is created. Any build-up of fabric as a consequence of the longitudinal seam 18 should be situated such that the build-up does not lie against the skin when the sleeve body 5 is pulled onto the limb. That is, the sleeve is first drawn on "inside out" with the seam exposed. To eliminate the longitudinal seam it may be possible to form the sleeve body 5 by weaving the fabric in a tubular form in the same manner in which socks are manufactured today. However, it is not known if the preferred fabrics, discussed below, are available presently in this form.

The first end opening 15 incorporates a closure means for drawing the sleeve body 5 snugly to the arm and thereby maintaining the sleeve body 5 in position. One example of such closure means is an elastic band 20 sewn into a hem of the sleeve body 5 as shown in FIG. 1. Other closure means will be obvious to those skilled in working with such materials and may also be used to accomplish the same function. One such is a draw string. Another is overlapping tabs with snaps or VELCRO® style fasteners. To some extent elasticity of the sleeve body 5 fabric itself will act as a closure means.

Figure 2:
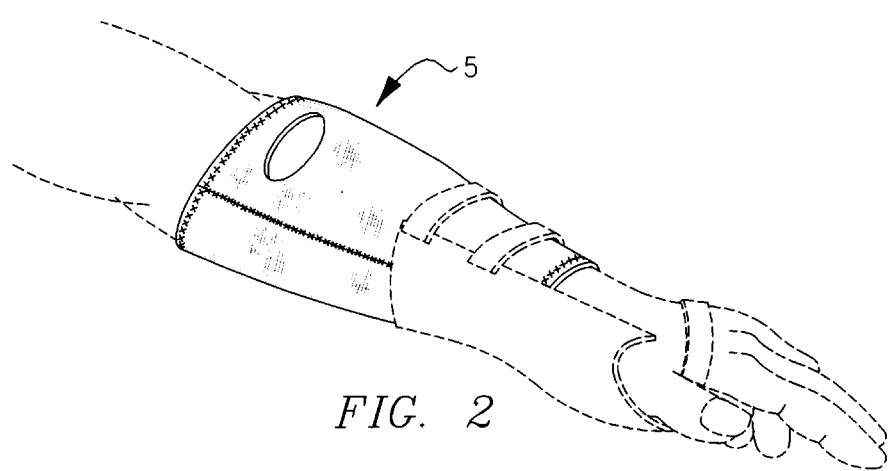
FIG. 2 shows a medical splint secured over the embodiment of FIG. 1. The sleeve body cover portion has not yet been drawn over the splint.
Figure 3:
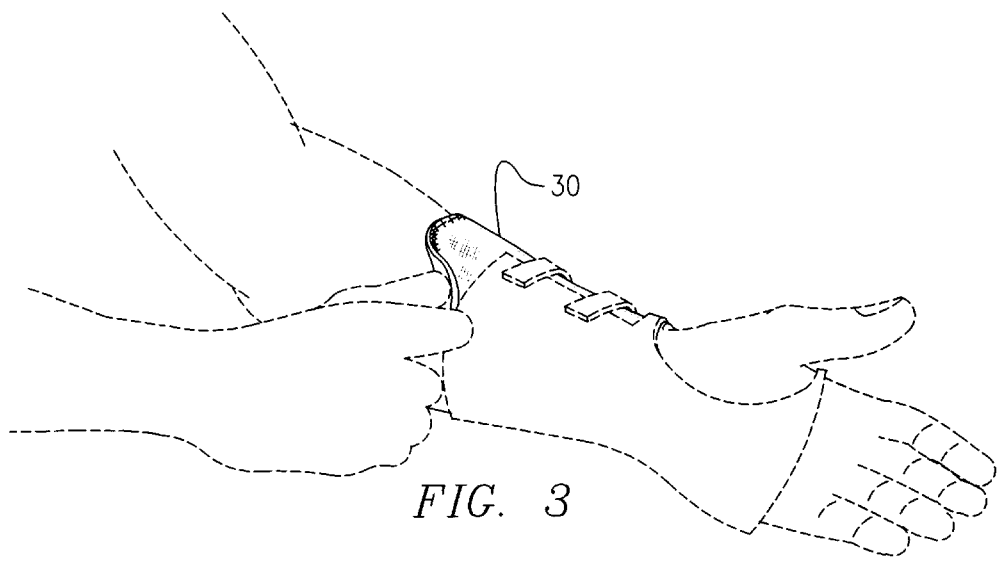
FIG. 3 shows the embodiment of FIG. 1 as it is drawn over the splint.

FIG. 2 shows how a wrist splint 6 is attached over a sleeve body 5. After the support device is positioned over the liner portion 10 of the sleeve body 5 and secured, the remaining length of the sleeve body 5 is then pulled back over the top of the support device thereby covering it with a cover portion 30. The liner and cover portions 10,30 are approximately equal in length. FIG. 3 shows this embodiment of the invention as the cover portion 30 is drawn over a wrist splint.

Figure 4:
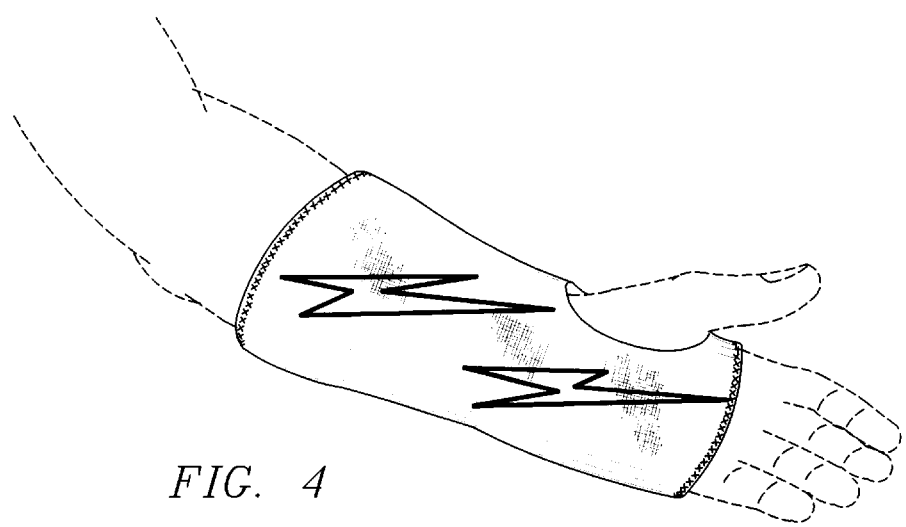
FIG. 4 shows the embodiment of FIG. 1 in its final configuration covering a medical splint.

The sleeve body 5 second end opening 25 incorporates a closure means similar to that described on the first end opening 15. After the sleeve body 5 is drawn and pulled by the user over the end of the support device and released, the closure means draws the cover portion 30 over the end of the support device such that the sleeve body second end opening 25 is secured in this position. The closure means reduces the circumference of the opening 25 to less than that of the support device such that the sleeve body cover portion 30 is prevented from withdrawing and uncovering the support device.

Where the invention is to be used in conjunction with a forearm support device, a loop 35 is secured to the second end opening 25 or, alternatively incorporated within the sleeve body 5. In this embodiment, after the cover portion 30 is drawn over the support device, the loop 35 is placed over the thumb or finger of the user's hand to maintain the position of the cover portion 30. The loop 35 may be formed of a band or hoop of material secured to the second end opening 25. Preferably, the loop 35 is formed within the sleeve body 5 by cutting a hole 40 in the sleeve body 5 adjacent to the second end opening 25, leaving a strap portion 45 of material between this and the second end opening 25. The width of the strap portion 45 from the perimeter of the hole 40 to the second end opening 25 is preferably 2 to 2.5 inches. The strap portion 45 of material then forms a loop 35 as it is drawn over the thumb which is inserted through the hole 40. The loop 35 is preferably located opposite the circumferential position of the longitudinal seam 18. This loop location will position the seam, in use, on a relatively less sensitive part of the user's arm. For the sake of clarity, the loop location, relative to the seam, is not shown in the preferred position in the figures. It will be obvious to one skilled in the art to reinforce such a hole 40 by such methods as stitching or otherwise securing additional material about the perimeter of the hole 40. In this way the sleeve body 5 surrounding the hole 40 will have added durability. FIG. 4 shows the invention as completely installed with a wrist splint. The splint is completely covered and hidden and the sleeve body 5 graphic design 11 prominent.

In an alternative embodiment the loop 35 is absent. Where a support device is to be used over a portion of a limb other than the forearm, the loop 35 cannot be used to help secure the sleeve body 5 as previously described. In these circumstances the second end opening 25 is retained in place solely a the closure means such as the elastic band 20 previously described.

The sleeve body 5 is formed of a lightweight fabric that is comfortable against the skin, assists elimination of perspiration, and creates a form-fitting and attractive appearance. Natural fabrics such as cotton have been known to be generally preferred where comfort is desired. However, all-cotton fabrics are neither durable nor sufficiently stable for the present invention. Cotton/elastomeric fabrics incorporating cotton fibers and elastomeric fiber material such as that commonly known as cotton-LYCRA® have been found to provide unique advantages in construction of support device liners and covers. Unlike other fabrics such as an all-cotton fabric, LYCRA® fabrics have sufficient strength and elasticity to fit snugly to the arm even when wet and despite movement of an overlying support device. As a consequence the fabric does not bunch against the arm but retains its shape and comfort. LYCRA® is commercially available in a variety of fabric blends such as with nylon fiber as well as with cotton fiber. However, the different LYCRA® fabrics vary greatly in their texture, nylon blends being more hard and slick as well as having a reduced moisture absorption capability as compared to cotton-LYCRA®. Cotton-LYCRA®, which uses a substantial cotton fiber content, provides both a preferred texture and feel as well as better moisture absorption. Additionally, experiments have shown that the combination of stretch and fabric texture particular to cotton-LYCRA® when used as a cover as in the present invention grip the skin to help retain a support device in place on the user's limb. The slickness of other LYCRA® blends does not provide this benefit. LYCRA® is currently used in a variety of sport clothing applications where comfort is required. LYCRA® is available in many colors and designs which allows for a multiple of graphic images that may be created on the sleeve body 5. In the future, as new fabrics are developed, those meeting the above characteristics may also be advantageously applied to the invention. Because the length of medical support devices and non-medical support devices vary depending on many factors including the function of the support device and size of the person, commercial embodiments of the invention should be made available in multiple sizes. However, the use of elastomeric fabrics will, again, be a benefit as the stretchability will allow a greater range of use for each size.

Although in the drawings the invention is shown used over a medical support device on an arm, its construction and application is essentially the same when used to cover medical support devices used on upper arm and leg, or leg and arm joints. Where the invention is used to cover an elbow or knee support device, the use of elastomeric fabrics are particularly important. Because the shape of the joint support device changes with the attitude of the limbs, only an elastomeric fabric will provide the "give" or flexibility to allow motion while maintaining a snug fit.

Figure 5:
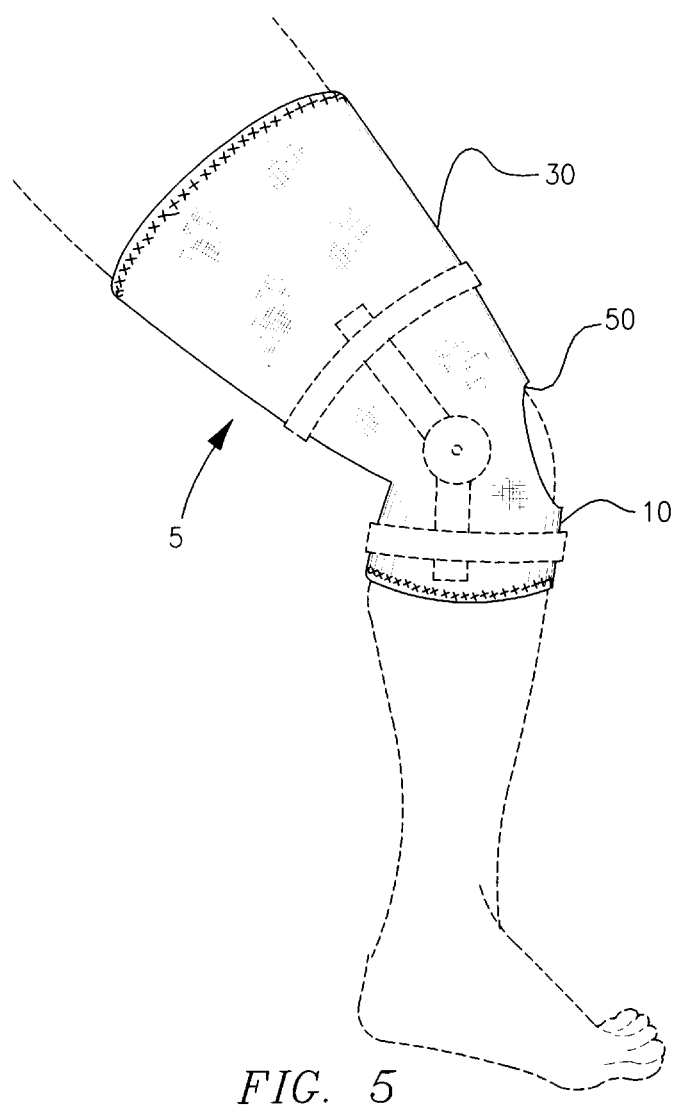
FIG. 5 shows another embodiment on the invention drawn over a knee joint.

FIG. 5 shows one embodiment of the invention worn over a knee. A knee brace has been installed over the sleeve body 5 liner portion 10; the cover portion 30 has not yet been drawn back. A cutout 50 is shown in the sleeve body 5 located generally in the middle of the liner portion 30.

Compressive outer garments are prescribed by doctors at times to treat medical conditions involving burns, scarring, and circulatory problems as well as others. A LYCRA® type fabric in the present invention can provide such a compression. For such use the sleeve body is formed with sufficiently small circumference to provide an effective compression when drawn on a limb. The particular dimensions necessary to create an effective compression will be dependent upon the particular fabric used, its elasticity, and the nature of the condition to be treated.

The invention is applied similarly to non-medical sport pads such as rollerskate pads worn on the arms and legs for protection in falls while traveling on roller skates. These pads are typically foam filled fabric, essentially tube-like in shape, which are either pulled over the arm or leg or have a longitudinal opening and are attached by securing closures such as loop-and-hook (VELCRO®) fastener. Both the materials and closure used may be sources of discomfort to the wearer. The particular features of comfort, physical protection of the covered support device and enhanced appearance are equally important in this use.

While specific embodiments of the invention are described above, they illustrate, and are not limiting of, the scope of the invention. Other embodiments will be obvious to those skilled in the art and are intended to be within the scope of the invention as claimed below. Other products, materials and methods existing and to be found in the future may be equally and obviously applicable and are also considered within the scope of the claimed invention.

I claim:

1. An integral sleeve and cover providing improved comfort and appearance to wearers of medical support devices and sports pads, comprising;

a tubular sleeve body formed substantially of cotton and elastomeric fibers, said sleeve body having a lining portion and a cover portion and having a first and second end each said end forming an opening, said sleeve body being formed of a generally rectangular shaped fabric piece having two opposing sides, said opposing sides being joined by a longitudinal seam, said sleeve body also having a predetermined length from said first end to said second end, said length being essentially double the length of a typical support device, and a loop formed within said sleeve body, such that in use said sleeve body may be disposed over a person's forearm, a typical support device secured over the sleeve body lining portion and the sleeve body cover portion then drawn over the support device thereby covering it.

2. An integral sleeve and cover kit providing improved comfort and appearance to wearers of medical support devices and sports pads comprising;

a support device for wearing on a human limb, said support device having a predetermined length, a tubular sleeve body formed substantially of cotton and elastomeric fibers, said sleeve body having a lining portion and a cover portion and having a first and second end each said end forming an opening, said sleeve body having a predetermined length from said first end to said second end, said length being essentially double the length of said support device, and a loop formed within said sleeve body, such that in use said sleeve body may be disposed over a wearer's limb, the support device secured over the sleeve body lining portion and the sleeve body cover portion then drawn over the support device thereby covering it.

3. A support device and sleeve providing enhanced comfort and improved appearance comprising:

a tubular sleeve body;

a support device designed to be worn over a human limb;

said sleeve body having a liner portion, said liner portion being disposed beneath said support device;

said sleeve body also having a cover portion, said cover portion substantially covering said support device, said cover portion being integrally connected to said liner portion;

said sleeve body being formed substantially of cotton and elastomeric fibers, said fabric being sufficiently thin and elastic to allow said cover portion to fit snugly over said support device in a form-fitting fashion;

thereby creating in use on a wearer's limb a comfort improving barrier between the support device and the limb and also creating a neat and esthetically pleasing outer appearance.

* * * * *